US008121797B2

(12) United States Patent
Heckerman et al.

(10) Patent No.: US 8,121,797 B2
(45) Date of Patent: Feb. 21, 2012

(54) T-CELL EPITOPE PREDICTION

(75) Inventors: David E. Heckerman, Bellevue, WA (US); Carl M. Kadie, Bellevue, WA (US); Jennifer Listgarten, Redmond, WA (US); Noah Aaron Zaitlen, Venice, CA (US); Nebojsa Jojic, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 112 days.

(21) Appl. No.: 11/963,081

(22) Filed: Dec. 21, 2007

(65) Prior Publication Data

US 2008/0172215 A1 Jul. 17, 2008

Related U.S. Application Data

(63) Continuation-in-part of application No. 11/622,895, filed on Jan. 12, 2007, and a continuation-in-part of application No. 11/770,684, filed on Jun. 28, 2007.

(51) Int. Cl.
*G01N 33/50* (2006.01)
(52) U.S. Cl. ............................................ 702/20; 703/11
(58) Field of Classification Search ........................ None
See application file for complete search history.

(56) References Cited

U.S. PATENT DOCUMENTS

| | | | |
|---|---|---|---|
| 5,933,819 A | 8/1999 | Skolnick et al. |
| 6,861,234 B1 | 3/2005 | Simard et al. |
| 6,895,396 B2 | 5/2005 | Schwartz et al. |
| 7,094,555 B2 | 8/2006 | Kwok et al. |
| 2004/0072162 A1 | 4/2004 | Fomsagaard et al. |
| 2004/0072246 A1 | 4/2004 | Martin et al. |
| 2004/0072249 A1 | 4/2004 | Hoffman et al. |
| 2004/0137537 A1 | 7/2004 | Montero-Julian et al. |
| 2005/0074809 A1 | 4/2005 | Brusic |
| 2005/0074813 A1 | 4/2005 | Nauss et al. |
| 2005/0079549 A1 | 4/2005 | Castracane |
| 2005/0095655 A1 | 5/2005 | Montero-Julian et al. |
| 2006/0057673 A1 | 3/2006 | Liu et al. |
| 2006/0084116 A1 | 4/2006 | Muchhal |
| 2006/0111554 A1 | 5/2006 | Lasters et al. |
| 2006/0160071 A1 | 7/2006 | Heckerman et al. |
| 2006/0257944 A1 | 11/2006 | Fridman et al. |
| 2007/0005262 A1 | 1/2007 | Gershoni et al. |
| 2007/0154953 A1 | 7/2007 | Brunner et al. |

FOREIGN PATENT DOCUMENTS

| | | |
|---|---|---|
| WO | WO9859244 A1 | 12/1998 |
| WO | WO0220564 A2 | 3/2002 |
| WO | WO2005038429 A2 | 4/2005 |

OTHER PUBLICATIONS

Heckerman et al. (A. Apostolico et al. (Eds.): RECOMB 2006, LNBI 3909, pp. 296-308, 2006).*
Brusic et al. (Bioinformatics, vol. 14, No. 2, p. 121-130, 1998).*
Tandon et al. (Proceedings of the 2005 IEEE Computational Systems Bioinformatics Conference Workshops (CSBW'05), pp. 1-2).*
Rousseeuw et al. (Computational Statistics & Data Analysis 43 (2003) 315-332).*
Williams et al. (ACM International Conference Proceeding Series; vol. 119, Proceedings of the 22nd international conference on Machine learning, Bonn, Germany, pp. 972-979, 2005).*
Lee et al. (Proceedings of the Twentieth International Conference on Machine Learning (ICML-2003), Washington DC, 2003).*
Bhasin et al. (Nucleic Acids Research, vol. 33, W202-W207, 2005).*
Peters et al. (PLOS Biology, vol. 3, No. 3, e91, p. 379-381, 2005).*
Laurent Jacob, et al. Epitope prediction improved by multitask support vector machines. Feb. 6, 2007. http://cg.ensmp.fr/~jacob/documents/mtkepitope-jacob-vert.pdf.
Yuanyuan Xiao, et al. Prediction of Genomewide Conserved Epitope Profiles of HIV-1: Classifier Choice and Peptide Representation. http://repositories.cdlib.org/cgi/viewcontent.cgi?article=1022&context=cbmb. Last accessed on Aug. 9, 2007.
Vladimir Brusic, et al. Prediction of promiscuous peptides that bind HLA class I molecules. Feb. 14, 2002. http://sdmc.i2r.a-star.edu.sg/iaamsad/papers/ICB280-2002.pdf.
Morten Nielsen, et al. Reliable prediction of T-cell epitopes using neural networks with novel sequence representations. Aug. 10, 2007. http://www.proteinscience.org/cgi/reprint/12/5/1007.pdf.
Jain, "Scoring Noncovalent Protein-Ligand Interactions: A Continuous Differentiable Function Tuned to Compute Binding Affinities", Springer Netherlands, Journal of Computer-Aided Molecular Design, 1996, vol. 10, No. 5, pp. 427-440.
Jurs, et al., "Studies of Chemical Structure-Biological Activity Relations Using Pattern Recognition", ACS, Computer-Assisted Drug Design, 1979, Chapter 4, pp. 103-129.
Qu, et al., "Bayesian Protein Family Classifier", AAAI Press, In the Proceedings of the 6th International Conference on Intelligent Systems for Molecular Biology, 1998, pp. 131-139 (9 pgs.).
Altuvia, et al., "A Structure-Based Approach for Prediction of MHC-Binding Peptides", Elsevier Inc., Methods, Bioinformatics in Vaccine Design, 2004, vol. 34, Issue 4, pp. 454-459.
Altuvia, et al., "A Structure-Based Algorithm to Predict Potential Binding Peptides to MHC Molecules with Hydrophobic Binding Pockets", Elsevier Science Inc., Human Immunology, Nov. 1997, vol. 58, Issue 1, pp. 1-11.
Arien, et al., "Replicative Fitness of Historical and Recent HIV-1 Isolates Suggests HIV-1 Attenuation Over Time", Lippincott Williams & Wilkins, AIDS, 2005, vol. 19, Issue 15, pp. 1555-1564.

(Continued)

*Primary Examiner* — Karlheinz R Skowronek
(74) *Attorney, Agent, or Firm* — Lee & Hayes, PLLC

(57) ABSTRACT

Epitope prediction models are described herein. By way of example, a system for predicting epitope information relating to a epitope can include a classification model (e.g., logistic regression model). The trained classification model can illustratively operatively execute one ore logistic functions on received protein data, and incorporate one or more of hidden binary variables and shift variables that when processed represent the identification (e.g., prediction) of one or more desired epitopes. The classification model can be configured to predict the epitope information by processing data including various features of an epitope, MHC, MHC supertype, and Boolean combinations thereof.

20 Claims, 12 Drawing Sheets

OTHER PUBLICATIONS

Bhasin, et al., "MHCBN: A Comprehensive Database of MHC Binding and Non-Binding Peptides", Oxford University Press, Bioinformatics, 2003, vol. 19, No. 5, pp. 665-666.

Brusic, et al., "Prediction of MHC Binding Peptides Using Artificial Neural Networks", Complexity International, Apr. 1995, vol. 2, pp. 1-10 (In Complex Systems: Mechanism of Adaptation, IOS Press, Amsterdam, 1994, pp. 253-260).

Chang, et al., "Predicting Peptides Bound to I-Ag7 Class II Histocompatibility Molecules Using a Novel Expectation-Maximizaton Alignment Algorithm", Wiley-VCH, Proteomics, 2007, vol. 7, Issue 3, pp. 367-377.

Davies, et al., "A Novel Predictive Technique for the MHC Class II Peptide-Binding Interaction", Molecular Medicine, 2003, vol. 9, Nos. 9-12, pp. 220-225.

Deng, et al., "Predicting Protein-Ligand Binding Affinities Using Novel Geometrical Descriptors and Machine-Learning Methods", American Chemical Society, Journal of Chemical Information and Computer Sciences, 2004, vol. 44, No. 2, pp. 699-703.

Density, Elsevier Science/Academic Press, CREDO Reference, 1992, Retrieved on Jun. 25, 2008 at <<http://www.xreferplus.com/entrypp.jsp?xrefid=3094286&secid=.->>, 1 pg.

Freire, "Thermodynamics of Protein Folding and Molecular Recognition", IUPAC, Pure and Applied Chemistry, 1997, vol. 69, Issue 11, pp. 2253-2261 (In the 14th Internationsl Conference on Chemical Thermodynamics, Toyonaka, Osaka, JP, Aug. 25-30, 1996).

Guler, "A Model with an Intrinsic Property of Learning Higher Order Correlations", Elsevier Science Ltd., Neural Networks, 2001, vol. 14, Issues 4-5, pp. 495-504.

Hertz, et al., "PepDist: A New Framework for Protein-Peptide Binding Prediction Based on Learning Peptide Distance Functions", BMC Bioinformatics, 2006, vol. 7, Suppl. 1, 21 pgs.

Holmes, et al., "An Expectation Maximization Algorithm for Training Hidden Substitution Models", Elsevier Science Ltd., Journal of Molecular Biology, 2002, vol. 317, Issue 5, pp. 753-764.

International Search Report and Written Opinion dated Oct. 8, 2008 for PCT Application Serial No. PCT/US2008/060945, 11 pgs.

Jojic, et al., "Learning MHC I-Peptide Binding", Oxford University Press, Bioinformatics, 2006, vol. 22, Issue 14, pp. e227-e235.

Jojic, et al., "Topographic Transformation as a Discrete Latent Variable", MIT Press, In Advances in Neural Information Processing Systems 12, 2000, 7 pgs.

Jojic, et al., "Using 'epitomes' to Model Genetic Diversity: Rational Design of HIV Vaccine Cocktails", Microsoft Research, In the Proceedings of the 19th Annual Conference on Neural Information Processing Systems, Dec. 5-10, 2005, 8 pgs.

Jones, et al., "A New Approach to Protein Fold Recognition", Nature, 1992, vol. 358, pp. 86-89.

Karpenko, et al., "Prediction of MHC Class II Binders Using the Ant Colony Search Strategy", Elsevier, Artificial Intelligence in Medicine, 2005, vol. 35, Issue 1, pp. 147-156.

Kratochwil, et al., "Predicting Plasma Protein Binding of Drugs: a New Approach", Elsevier Science Inc., Biochemical Pharmacology, 2002, vol. 64, Issue 9, pp. 1355-1374.

Lazaridis, et al., "Effective Energy Functions for Protein Structure Prediction", Elsevier Science Ltd., Current Opinion in Structural Biology, 2000, vol. 10, Issue 2, pp. 139-145.

Lee, et al., "Protein Structure Prediction Based on Fragment Assembly and Parameter Optimization", Elsevier B.V., Biophysical Chemistry, 2005, vol. 115, Issues 2-3, pp. 209-214.

Lilien, et al., "A Novel Ensemble-Based Scoring and Search Algorithm for Protein Redesign, and its Application to Modify the Substrate Specificity of the Gramicidin Synthetase a Phenylalanine Adenylation Enzyme", ACM, In the Proceedings of the Eighth Annual International Conference on Research in Computational Molecular Biology, 2004, pp. 46-57.

Mamitsuka, "Predicting Peptides That Bind to MHC Molecules Using Supervised Learning of Hidden Markov Models", Wiley-Liss Inc., Proteins: Structure, Function, and Genetics, 1998, vol. 33, Issue 4, pp. 460-474.

Marshall, et al., "Protein-Protein Docking Methods", Springer US, Proteomics and Protein-Protein Interactions, Protein Reviews, 2005, vol. 3, pp. 115-146.

Melo, et al., "Statistical Potentials for Fold Assessment", Protein Science, 2002, vol. 11, pp. 430-448.

Miyazawa, et al., "Residue-Residue Potentials with a Favorable Contact Pair Term and an Unfavorable High Packing Density Term, for Simulation and Threading", Academic Press, Journal of Molecular Biology, 1996, vol. 256, Issue 3, pp. 623-644.

Moore, et al., "Evidence of HIV-1 Adaptation to HLA-Restricted Immune Responses at a Population Level", Science, May 24, 2002, vol. 296, No. 5572, pp. 1439-1443.

Murugan, et al., "Prediction of MHC Class II Binding Peptides Based on an Iterative Learning Model", Immunome Research, 2005, vol. 1, No. 6, 10 pgs.

Neal, "Bayesian Methods for Machine Learning", In the Eighteenth Annual Conference on Neural Information Processing Systems, 2004, NIPS 2004 Tutorial, 67 pgs.

Neilsen, et al., "Improved Prediction of MHC Class I and Class II Epitopes Using a Novel Gibbs Sampling Approach", Oxford University Press, Bioinformatics, 2004, vol. 20, No. 9, pp. 1388-1397.

Office Action mailed Jul. 7, 2008 for U.S. Appl. No. 11/356,196, 22 pages.

Park, et al., "Toward an Energy Function for the Contact Map Representation of Proteins", John Wiley & Sons Inc., Proteins, 2000, vol. 40, No. 2, pp. 237-248.

Peters, et al., "A Community Resource Benchmarking Predictions of Peptide Binding to MHC-I Molecules", PLoS Computational Biology, Jun. 2006, vol. 2, Issue 6: e65, pp. 0574-0584.

Rammensee, et al., "SYFPEITHI: Database for MHC Ligands and Peptide Motifs", Springer Berlin/Heidelberg, Immunogenetics, Nov. 1999, vol. 50, Nos. 3-4, pp. 213-219.

Reche, "Enhancement to the RANKPEP Resource for the Prediction of Peptide Binding to MHC Molecules Using Profiles", Springer Berlin/Heidelberg, Immunogenetics, Biomedical and Life Sciences, 2004, vol. 56, No. 6, pp. 405-419.

Schueler-Ferman, et al., "Structure-Based Prediction of Binding Peptides to MHC Class I Molecules: Application to a Broad Range of MHC Alleles", Cambridge University Press, The Protein Society, Protein Science, 2000, vol. 9, Issue 9, pp. 1838-1846.

Sette, et al., "Nine Major HLA Class I Supertypes Account for the Vast Preponderance of HLA-A and -B Polymorphism", Springer-Verlag, 1999, Immunogenetics, vol. 50, pp. 201-212.

Sette, et al., "Peptide Binding to the Most Frequent HLA-A Class I Alleles Measured by Quantitative Molecular Binding Assays", Elsevier Ltd., Molecular Immunology, Aug. 1994, vol. 31, Issue 11, pp. 813-822.

Singh, et al., "ProPed: Prediction of HLA-DR Binding Sites", Oxford University Press, Bioinformatics, 2001, vol. 17, No. 12, pp. 1236-1237.

Specific Weight, Elsevier Science/Academic Press, CREDO Reference, 1992, Retrieved on Jun. 25, 2008 at <<http://www.xreferplus.com/entrypp.jsp?xrefid=3161132&secid=.->>, 1 pg.

Stern, et al., "Peptide 15-mers of Defined Sequence that Substitute for Random Amino Acid Copolymers in Amelioration of Experimental Autoimmune Encephalomyelitis", In the Proceedings of the National Academy of Sciences, 2005, vol. 102, No. 5, pp. 1620-1625.

Swain, et al., "An Automated Approach to Modelling Class II MHC Alleles and Predicting Peptide Binding", IEEE, In the Proceedings of the IEEE 2nd International Symposium on Bioinformatics and Bioengineering, 2001, pp. 81-88 (9 pgs.).

Wiesmuller, et al., "Peptide Vaccines and Peptide Libraries", Biological Chemistry, Apr. 2001, vol. 382, Issue 4, pp. 571-579.

Wojciechowski, et al., "Docking of Small Ligands to Low-Resolution and Theoretically Predicted Receptor Structures", Wiley Periodicals Inc., Journal of Computational Chemistry, Recent Advances in Computational Biological Chemistry, 2001, vol. 23, Issue 1, pp. 189-197.

Yanover, et al., "Predicting Protein-Peptide Binding Affinity by Learning Peptide-Peptide Distance Functions", Springer Berlin/Heidelberg, Lecture Notes in Computer Science, Research in Computational Molecular Biology, 2005, vol. 3500, pp. 456-471.

Zhang, et al., "Consistency in Structural Energetics of Protein Folding and Peptide Recognition", The Protein Society, Protein Science, 1997, vol. 6, Issue 5, pp. 1057-1064.

Zhao, et al., "Application of Support Vector Machines for T-Cell Epitopes Prediction", Oxford University Press, Bioinformatics, 2003, vol. 19, No. 15, pp. 1978-1984.

Zhu, et al., "Improving Prediction of MHC Class I Binding Peptides with Additional Binding Data", Retrieved on Jan. 24, 2007, Available at <<http://www.jsbi.org/journal/GIW04/GIW04P127.pdf>>, 2 pgs.

Florea, et al., "Epitope Prediction Algorithms for Peptide-based Vaccine Design", Computer Society, In the Proceedings of the Computational Systems bioinformatics, 2003, 10 pages.

Gotoh, "Multiple Sequence Alignment: Algorithms and Applications", Advanced Biophysics, 1999, vol. 36, pp. 159-206.

Lund, et al., "Definition of Supertypes for HLA Molecules Using Clustering of Specificity Matrices", Immunogenetics, vol. 55, No. 12, 2004, pp. 797-810.

Panchenko et al., "Combination of Threading Potentials and Sequence Profiles Improves Fold Recognition", Journal of Molecular Biology 296, 2000, 13 pages.

Schmidler et al., "Bayesian Segmentation of Protein Secondary Structure", Journal of Computational Biology, vol. 7, Nos. 1/2, 2000, pp. 233-248.

Tsuda, et al., "Marginalized Kernels for Biological Sequences", Bioinformatics, 2002, vol. 18, Supplement 1, pp. S268-S275.

Bilenko, et al., "Adaptive Duplicate Detection Using Learnable String Similarity Measures", In the Proceedings of the Ninth ACM SIGKDD International Conference on Knowledge Discovery and Data Mining, 2003, pp. 39-48.

Chakrabarti, et al., "Dissecting Protein-Protein Recognition Sites", Wiley-Liss Inc., Proteins: Structure, Function, and Bioinformatics, vol. 47, Issue 3, May 2002, pp. 334-343.

Espadaler et al., "Prediction of protein-protein interations using distant conservation of sequence patterns and structure relationships", Bioinformatics, vol. 21, No. 16, 2005, pp. #3360-pp. #3368.

Mallios, "Predicting Class II MHC/Peptide Multi-level Binding with an Iterative Stepwise Discriminant Analysis Meta-algorithm", Oxford University Press, Bioinformatics, vol. 17, No. 10, 2001, pp. 942-948.

Waterhouse, "Classification and Regression using Mixtures of Experts", PhD. Thesis, University of Cambridge, 1997, pp.#1-pp. #215.

* cited by examiner f1 110
f2 120
fn 130
LR 140
epitope ? 150
100

T-CELL EPITOPE PREDICTION

CROSS-REFERENCE TO RELATED APPLICATIONS

This application is a continuation-in-part (CIP) application of U.S. patent application Ser. No. 11/622,895 filed Jan. 12, 2007 [MSFTP1640US], entitled, "IDENTIFYING ASSOCIATIONS USING GRAPHICAL MODELS," and U.S. patent application Ser. No. 11/770,684 filed Jun. 28, 2007 [MSFTP1736US], entitled "CLUSTER MODELING, AND LEARNING CLUSTER SPECIFIC PARAMETERS OF AN ADAPTIVE DOUBLE THREADING MODEL," the entirety of these applications are, herein, incorporated by reference.

BACKGROUND

The search for correlations in many types of data, such as biological data, can be difficult if the data are not exchangeable or independent and identically distributed (IID). For example, a set of DNA or amino acid sequences are rarely exchangeable because they are derived from a phylogeny (e.g., an evolutionary tree). In other words, some sequences are very similar to each other but not to others due to their position in the evolutionary tree. This phylogenetic structure can confound the statistical identification of associations. For instance, although a number of candidate disease genes have been identified by genome wide association (GWA) studies, the inability to reproduce these results in other studies is likely due in part to confounding by phylogeny. Other areas in which phylogeny may confound the statistical identification of associations include the identification of coevolving residues in proteins given a multiple sequences alignment and the identification of Human Leukocyte Antigen (HLA) alleles that mediate escape mutations of the Human Immunodeficiency Virus (HIV).

The human adaptive immune response is composed of two core elements: antibody-mediated response (sometimes called humoral response), and T-cell-mediated response (sometimes called cellular response). To date, essentially human vaccines have been made by exploiting the underlying mechanisms of the antibody-mediated response, for example with diseases such as polio and measles. However, for these diseases, it was known that people could recover upon acquisition of humoral immunity. In contrast, for certain viruses—for example, HIV—there are no known documented cases of a person recovering from the infection, and it is highly unlikely that the same principles of vaccine design could be successfully applied in these cases. In particular, it is thought that vaccines for diseases such as HIV must prime the cellular immune response rather than or in addition to the humoral response.

Generally, cellular response mechanisms can be characterized by an ability of certain antigen-presenting cells to ingest and digest viral proteins into smaller peptides, and then to present these peptides, known as epitopes, at the surface of the cell. This process is mediated by HLA molecules which form a complex with the epitope before it is presented. The epitope/HLA complexes can then be recognized by a T-cell, thereby activating the T-cell to subsequently recognize and kill virally infected cells. Several types of T-cells exist, each playing its own role. In ongoing HIV vaccine research, the elicitation of a CD8+ T-cell response has shown promise.

T-cell epitopes are presented on the surface of an antigen-presenting cell, where they are bound to Major Histocompatibility Complex (MHC) molecules. T-cell epitopes presented by MHC class I molecules are typically peptides between 8 and 11 amino acid in lengths, while MHC class II molecules present longer peptides, and non-classical MHC molecules also present non-peptidic epitopes such as glycolipids.

Due to specificity in a number of sequential mechanisms, only certain epitopes are both presented at the surface of antigen-presenting cells and then subsequently recognized by T-cells. This specificity is determined in part by the sequence and properties of the presented epitope and by the genetic background (i.e., allelelic diversity) of the host (humans have up to six HLA class I alleles arising from the A, B and C loci). A crucial task in vaccine development is the identification of epitopes and the alleles that present them, since it is thought that a good vaccine will include a robust set of epitopes (robust in the sense of broad coverage and of covering regions that are essential for viral fitness in a given population characterized by a particular distribution of HLA alleles).

Because experiments required to prove that a peptide is an epitope for a particular HLA allele are time-consuming and expensive, epitope prediction can be of tremendous help in identifying new potential epitopes whose identity can then be confirmed experimentally. Beyond vaccine design, epitope prediction may have important applications such as predicting infectious disease susceptibility and transplantation success.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The subject matter described herein facilitates predicting information about epitopes. By way of example, a base model using logistic regression (LR) with feature selection can be illustratively employed to predict epitopes. Illustratively, the standard features used in epitope prediction include but are not limited to the identity (or supertype) of a Major Histocompatibility Complex (MHC) allele, the amino acid (or chemical property) of the amino acid at a certain position of the epitope and/or conjunctions of these features.

By way of another example, the subject matter includes machine learning techniques that employ the described base model having additional illustrative features and Boolean combinations thereof to improve epitope prediction. Illustratively, these additional features include but are not limited to the identity of the MHC or its supertype, the identity of an amino acid (or its chemical property) at a given position along the epitope, the identity of an amino acid (or its chemical property) at a given position along either region that flanks the epitope, the identity of an amino acid (or its chemical property) at a given position along the MHC molecule, and the binding energy of the peptide-HLA pair.

By way of another example, a predictive epitope platform can leverage a standard logistic regression model with the addition of one or more hidden variables that, illustratively operatively, can represent the presence or absence of supertypes among the MHC molecules. Such model can be learned with an exemplary expectation maximization algorithm containing a gradient optimization. Illustratively, the probability that a given peptide-MHC pair is an epitope can be determined via standard (exact) inference.

By way of another example, the herein described systems and methods can illustratively operate to predict epitopes for MHC class-II molecules. Illustratively, for MHC class-II prediction, the edges of the epitope can hang outside an MHC groove. A hidden variable (e.g., shift variable) can be expressed to represent the unknown position of the hanging epitope. Operatively, a modified LR model can be deployed wherein the variables of the model are conditioned on the expressed shift variable.

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents.

BRIEF DESCRIPTION OF THE DRAWINGS

Figure 1:
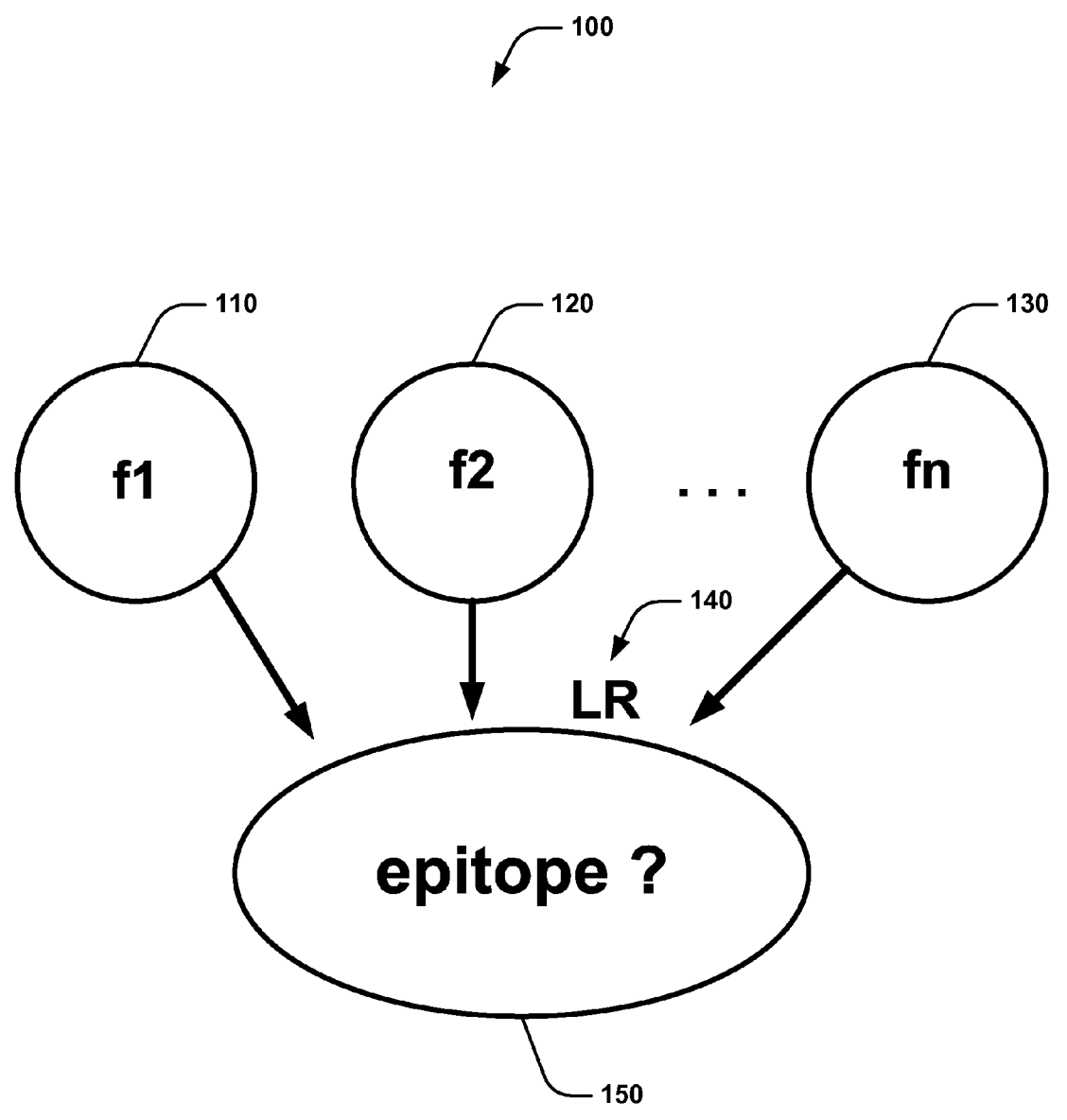

FIG. 1 is a block diagram of one example of a graphical model representing a standard logistic regression model.

FIG. 2 is a block diagram of one example of a graphical model representing a logistical regression model employing hidden variables.

DETAILED DESCRIPTION

Figure 3:
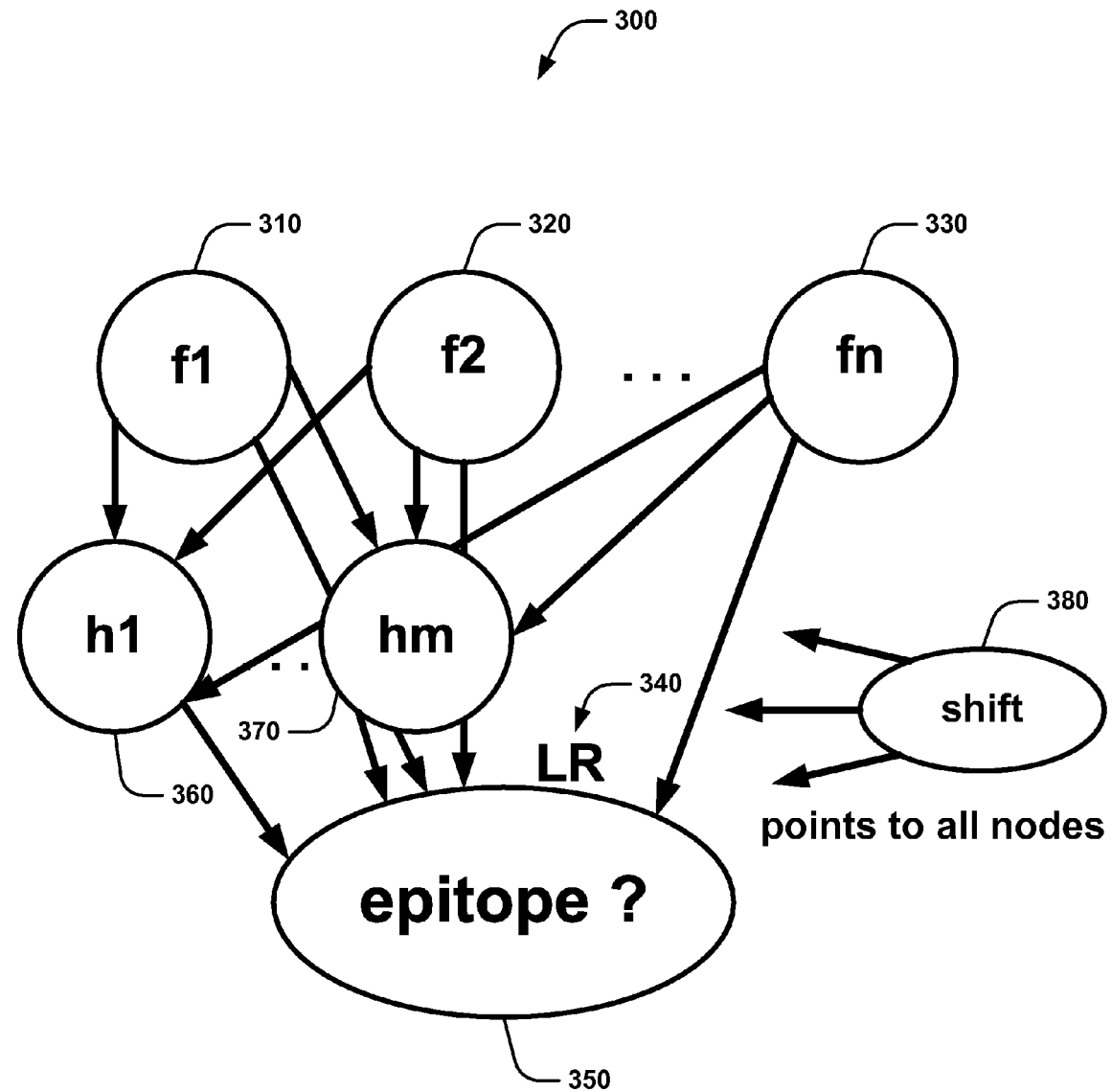
FIG. 3 is a block diagram of one example of a graphical model representing a logistic regression model employing a shift variable.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices are shown in block diagram form in order to facilitate describing the claimed subject matter.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface,", "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Artificial intelligence (AI) can be employed to identify a specific context or action, or generate a probability distribution of specific states of a system or behavior of a user without human intervention. Artificial intelligence relies on applying advanced mathematical algorithms—e.g., decision trees, neural networks, regression analysis, cluster analysis, genetic algorithm, and reinforced learning—to a set of available data (information) on the system or user.

Although the subject matter described herein may be described in the context of illustrative illustrations to predict epitopes the subject matter is not limited to these particular embodiments. Rather, the techniques described herein can be applied to any suitable type of epitope prediction methods, systems, platforms, and/or apparatus.

In an illustrative implementation, a logistic regression (LR) model for epitope prediction exploiting one or more special features can be employed providing several practical advantages: (1) the LR model is familiar to those skilled in the art with many readily-available implementations, (2) its output can be interpreted without difficulty, (3) training requires less memory than conventional epitope prediction models, (4) the parameters of LR given data have a single, globally optimal value that is easily learned, and (5) the LR model produces probabilities that tend to be well calibrated and hence useful for making decisions about (e.g.) whether to confirm a prediction in the lab (e.g., bench testing).

In an illustrative operation, the herein described systems and methods operate to leverage information across multiple HLA alleles to improve predictive accuracy for a specific allele. Illustratively, an epitope can be defined with respect to one or more HLA alleles. That is, a peptide which is an epitope for HLA-allele X may not also be an epitope for HLA-allele Y. Thus, epitope prediction takes as input both a peptide and an HLA allele, and returns the probability (or some score) reflecting how likely that pair is to be an epitope. HLA alleles can be encoded in a hierarchy, where extra digits are used to refer to more specific forms of the allele. For example, moving up the hierarchy from more specific to less specific forms of the allele can result in a set that includes A*020101, A*0201, and A02. Additionally, many 4-digit alleles can belong to a "supertype"; e.g., A*0201 belongs to the A2 supertype.

Typically, a single classifier is trained and tested for each HLA allele (where the allele is defined with respect to one specific level of the hierarchy) or for each HLA supertype. However, these approaches have several shortcomings. With such practices, classifiers can be only built for alleles with a large number of known epitopes or for alleles which fall in to one of the currently defined supertypes which is rather restrictive. Also, if an allele-specific or supertype-specific classifiers are built, then any information which could have been shared across somewhat similarly behaving alleles or supertypes is generally lost. Because sample sizes are usually extremely small, this shortcoming could be significant in some cases. With supertype classifiers, there exists a dependence upon current definitions of supertypes, which, with current practices, have not been rigorously tested in a quantitative way. It may also be the case that some information contained in epitopes is very general, not specific to either alleles or supertypes.

To ameliorate the shortcomings of existing practices, the herein disclosed subject matter considers simultaneously leveraging epitope information from a number of sources when making epitope predictions, such that in an illustrative operation to include: 1) within specific HLA alleles (as available and appropriate), 2) within specific HLA supertypes (as available and appropriate), 3) across all epitopes, regardless of supertype or allele (as appropriate).

That is, in predicting whether a peptide is an epitope for a given HLA allele, it is desirable to employ collateral epitope information not just information about epitopes for this allele, including but not limited to information about epitopes for other alleles within this allele's supertype (if it has one), and from information about other epitopes of any HLA type. Additionally, the herein described subject matter allows to automatically ascertain when each type of information is appropriate, and to what degree, allowing for optimize combinations to obtain epitope predictions in a principled manner.

In an illustrative implementation, these illustratively presented operations can be dependent on one or more selected epitope features that are employed and/or that all HLA alleles and supertypes are simultaneously trained with these features even though the herein described predictive model preferably operates to make predictions on whether a peptide is an epitope for a specific HLA allele.

In an illustrative operation, information across HLA alleles and supertypes are leveraged to derive a single model for all HLA alleles using illustrative features of the form (1) position N has a particular amino acid or chemical property and the epitope's HLA allele is Y (which when used alone would be roughly equivalent to simultaneously building separate models for each HLA allele), as well as (2) position N has a particular amino acid or chemical property and the epitope's HLA has supertype Y, which helps leverage information across HLA alleles for a given supertype, and (3) position N has a particular amino acid or position N has an amino acid with a particular chemical property, which helps leverage information across all HLA alleles and supertypes.

Illustratively, this leveraging approach can be applied to various classification models including logistic regression, support vector machines, and artificial neural networks. In our experiments, we show that our leveraging approach applied to logistic regression yields more accurate predictions than those generated from models learned on each supertype individually.

Classification Models (Logistic Regression Model):

It is appreciated that although the herein described subject matter is presented in the context of a logistic regression model, that such presentation is merely illustrative as the inventive concepts described herein can employ on or more classification models including but not limited to support vector machines and artificial neural networks.

By way of example, an exemplary logistic regression model can be described according to the following, y denotes the binary variable (or class label) to be predicted and $x=x_1, \ldots, x_k$ denote the binary (0/1) or continuous features to be used for prediction. In an illustrative implementation, y can correspond to whether or not a peptide-HLA pair is an epitope and the features correspond to 0/1 encodings of properties of the peptide-HLA pair. In this notation, the logistic regression model is:

$$\log\frac{p(y|x)}{1-p(y|x)} = w_0 + \sum_{i=1}^{k} w_i \cdot x_i$$

where $w=(w_0, \ldots, w_k)$ are the model parameters or weights. Given a data set of cases $(y^1,x^1), \ldots, (y^n,x^m)$ that are independent and identically distributed given the model parameters, the weights can be learned under an assumption that the weights are mutually independent, each having a Gaussian prior $p(w_i|\sigma^2)=N(0,\sigma^2)$, and determining the weights that have the maximum a posteriori (MAP) probability. That is, the weights that maximize the following quantity are determined.

$$\sum_{j=1}^{n} \log p(y^j | x^j, w) + \sum_{i=0}^{k} \log p(w_i | \sigma^2)$$

The illustrative optimization routine has a global maximum which can be found by a variety of techniques including gradient descent. In the illustrative implementation, $\sigma^2$ can be tuned using ten-fold cross validation on the training data.

Epitope Prediction:

FIG. 1 describes an exemplary epitope prediction environment 100 employing an illustrative conventional logistic regression model 140 to generate eptiope predictions 150. As is shown in FIG. 1, exemplary epitope prediction environment 100 is presented as an exemplary graphical model in which one or more logistic functions directed at processing HLA data such as f1 110, f2 120, up to fn 130 are deployed (e.g., to operate on input data representative of protein sequences, and more particularly, amino acid chains) as part of logistic regression model 140 to predict one or more desired epitopes 150.

In an illustrative operation, the exemplary classification model (e.g., LR model 140) employs one or more logistic functions f1 110, f2 120, up to fn 130 to process protein sequence data to identify HLA alleles. The exemplary logistic functions when executed generate a probability score of the location of desired epitopes (e.g., desirable to promote T-cell generation and deployment). In the illustrative operation, in addition to standard features used in predicting epitopes that include but are not limited to the identity (or supertype) of an MHC (HLA) allele, the amino acid/amino acid chemical property at a certain position of the epitope (and conjunctions of such features), one or more additional features can be utilized to improve epitope prediction. By way of example, such additional features can include but are not limited to the identity of an amino acid/amino acid chemical property at a given position along either region that flanks the epitope, and the identity of an amino acid/amino acid chemical property at a given position along the MHC molecule.

Figure 2:
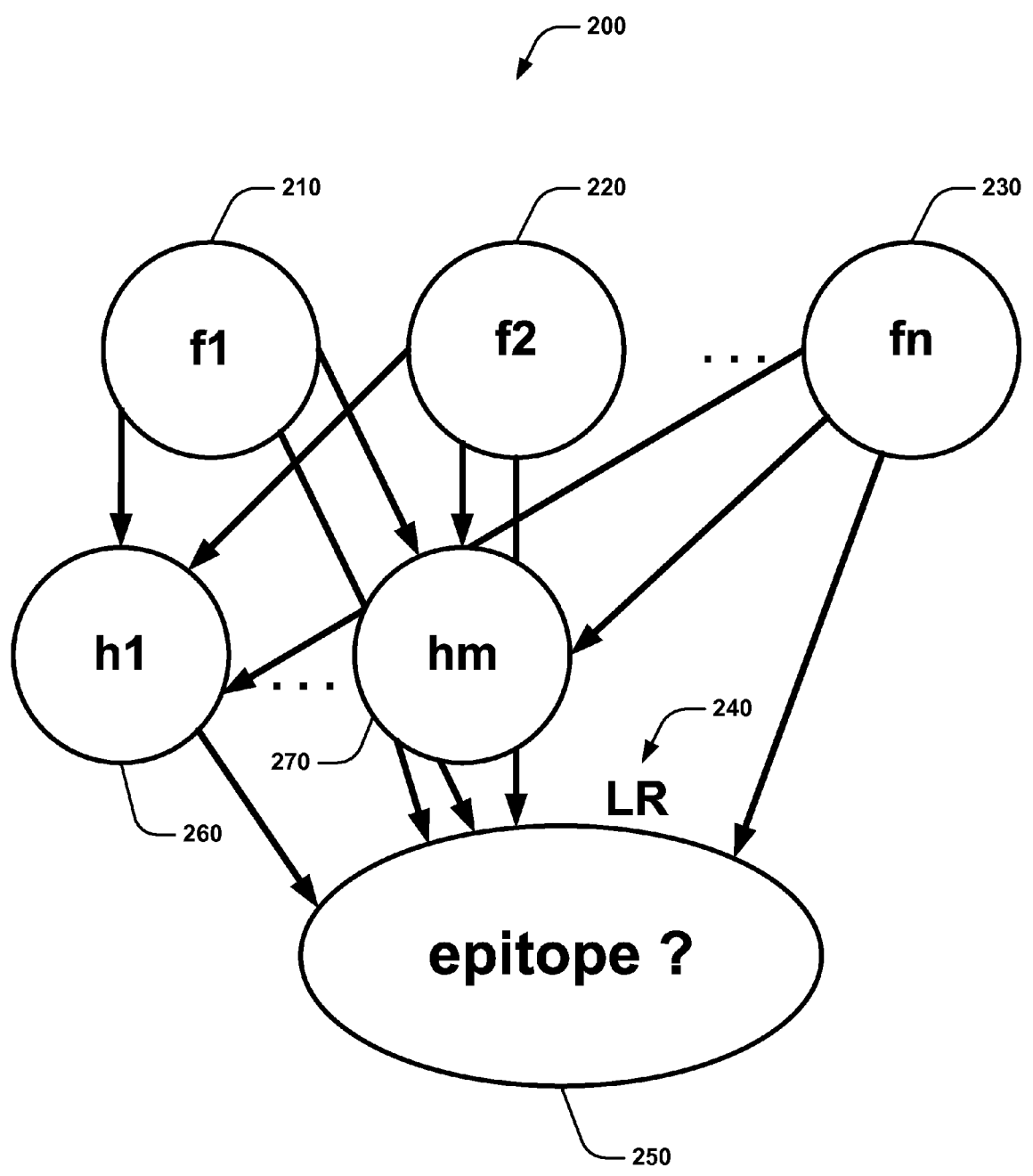

FIG. 2 describes another exemplary epitope prediction environment 200 employing an illustrative logistic regression model 240 that employ logistic functions, f1 210, f2 220 up to fn 230, and one or more hidden binary variables h1 260 up to hm 270 to generate epitope predictions 250. As is shown in FIG. 2, exemplary epitope prediction environment 200 is presented as an exemplary graphical model in which one or more logistic functions, f1 210, f2 220, up to fn 230, directed at processing HLA data have a many-to-many relationship with one or more binary hidden variables, h1 260 up to hm 270, such that when the one or more logistic functions 210, 220, up to 230, are executed by logistic regression model 240 additional collateral epitope data (e.g., learned MHC supertype data) is considered to generate a prediction of one or more desired epitopes 250.

In an illustrative operation, illustrative epitope prediction environment 200 can employ various hidden variables that represent the presence or absence of supertypes among the observed/processed MHC molecules. As can be appreciated by those skilled in the art, such a classification model (e.g., logistic regression model) can be learned with, for example, an expectation maximization (EM) algorithm in which the maximization step contains a gradient optimization (e.g., gradient descent).

FIG. 3 describes another exemplary epitope prediction environment 300 employing an illustrative logistic regression model 240 that employ logistic functions, f1 310, f2 320 up to fn 330, one or more hidden binary variables h1 360 up to hm 370, and a shift variable 380 to generate epitope predictions 350. As is shown in FIG. 3, exemplary epitope prediction environment 300 is presented as an exemplary graphical model in which one or more logistic functions, f1 310, f2 320, up to fn 330, directed at processing HLA data have a many-to-many relationship with one or more binary hidden variables, h1 360 up to hm 370, such that when the one or more logistic functions 310, 320, up to 330, are executed by logistic regression model 340 additional collateral epitope data (e.g., learned MHC supertype data) is considered to generate a prediction of one or more desired epitopes 350.

In an illustrative operation, illustrative epitope prediction environment 300 can employ various hidden variables that represent the presence or absence of supertypes among the observed/processed MHC molecules. Additionally, as is shown in FIG. 3, exemplary epitope prediction environment 300 can employ shift variable 380 to assist in predicting MHC class-II predictions. By way of example, for MHC class-II predictions, the edges of the epitope can hang outside the MHC groove. It is assumed that a single portion of a peptide within the groove leads to T-cell killing, shift variable 380 can be used to represent this unknown position. In the illustrative operation, the variables of the classification model are conditioned on the value of the shift variable to generate MHC class-II epitope predictions.

As can be appreciated by those skilled in the art, such a classification model (e.g., logistic regression model) using a shift variable can be learned with (e.g.) an EM algorithm in which the maximization step contains a gradient optimization (e.g., gradient descent).

Figure 4:
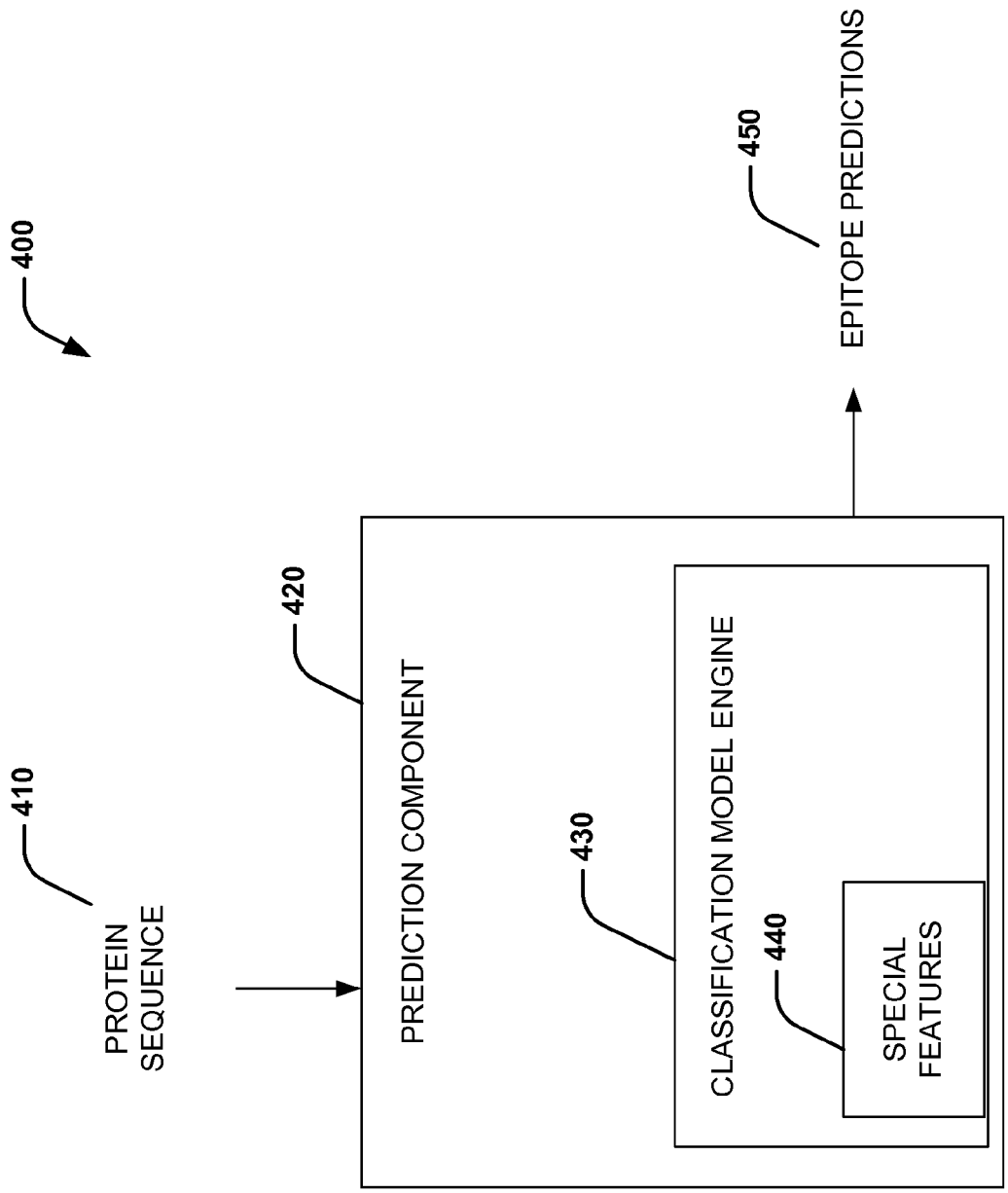
FIG. 4 is a block diagram of one example of a system for predicting epitopes according to a base logistic regression model.
Figure 5:
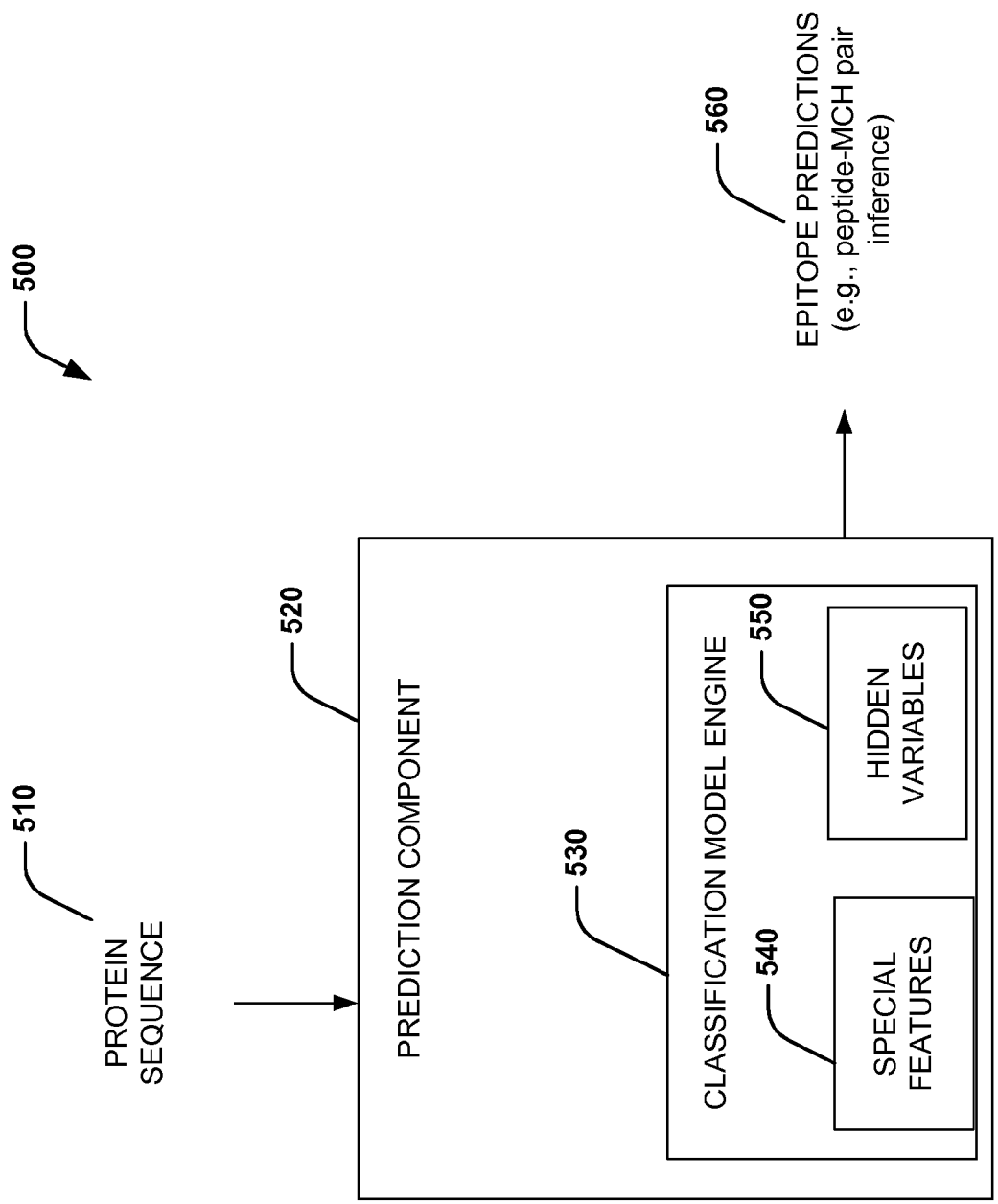
FIG. 5 is a block diagram of one example of a system for predicting epitopes according to a modified logistic regression model.

FIG. 4 schematically illustrates one example of a system 400 for use in predicting epitopes. As is shown in FIG. 5, system 400 comprises prediction component 420 having classification model engine 430 operating on special features 440. In an illustrative operation, prediction component 420 receives input data (e.g., protein sequence data 410) which is operatively processed by classification model engine 430 executing special features 440 to generate epitope prediction data 450.

In an illustrative implementation, classification model engine can comprise a computing environment executing one or more classification models including a logistic (LR) regression model. The LR model can exploit one or more special features when predicting epitopes including but are not limited to the identity of an amino acid/amino acid chemical property at a given position along either region that flanks the epitope, and the identity of an amino acid/amino acid chemical property at a given position along the MHC molecule.

FIG. 5 schematically illustrates another example of a system 500 for use in predicting epitopes. As is shown in FIG. 5, system 500 comprises prediction component 520 having classification model engine 530 operating on special features 540 and hidden variables 550. In an illustrative operation, prediction component 520 receives input data (e.g., protein sequence data 510) which is operatively processed by classification model engine 530 executing special features 540 and processing hidden variables 550 to generate epitope prediction data 560.

In an illustrative implementation, classification model engine can comprise a computing environment executing one or more classification models including a logistic (LR) regression model. The LR model can exploit one or more special features when predicting epitopes including but are not limited to the identity of an amino acid/amino acid chemical property at a given position along either region that flanks the epitope, and the identity of an amino acid/amino acid chemical property at a given position along the MHC molecule. In an illustrative operation, illustrative system 500 can employ various hidden variables 550 that represent the presence or absence of supertypes among the observed/processed MHC molecules.

Figure 6:
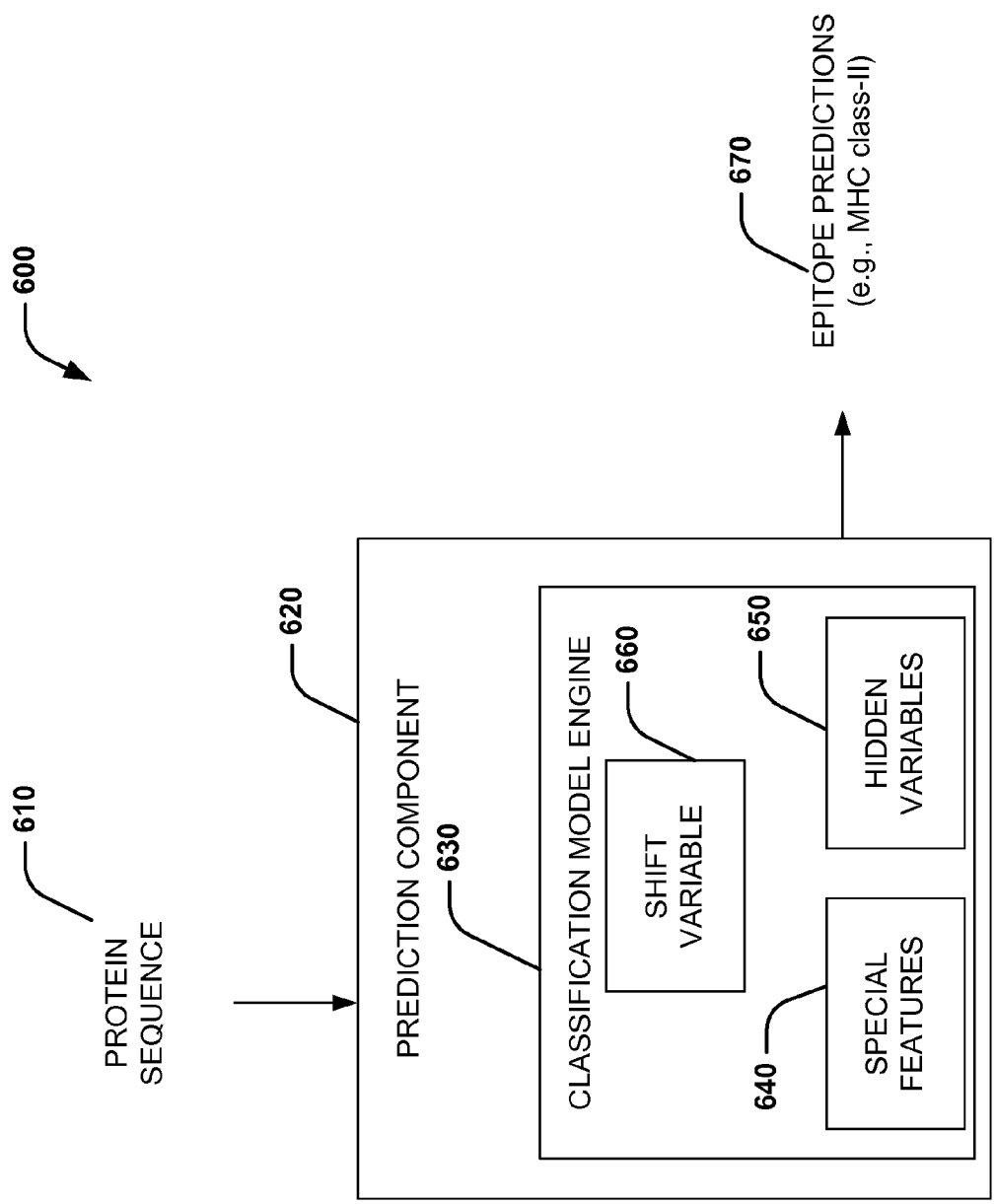
FIG. 6 is a block diagram of another example of a system for predicting epitopes according to a logistic regression model adapted to handle MHC class-II epitope predictions.

FIG. 6 schematically illustrates another example of a system 600 for use in predicting epitopes. As is shown in FIG. 6, system 600 comprises prediction component 620 having classification model engine 630 operating on special features 640, hidden variables 650, and shift variable 660. In an illustrative operation, prediction component 620 receives input data (e.g., protein sequence data 610) which is operatively processed by classification model engine 630 executing special features and processing hidden variables 650 and shift variable 660 to generate epitope prediction data 670.

In an illustrative implementation, classification model engine can comprise a computing environment executing one or more classification models including a logistic (LR) regression model. The LR model can exploit one or more special features when predicting epitopes including but are not limited to the identity of an amino acid/amino acid chemical property at a given position along either region that flanks the epitope, and the identity of an amino acid/amino acid chemical property at a given position along the MHC molecule. In an illustrative operation, illustrative system 600 can employ various hidden variables 650 that represent the presence or absence of supertypes among the observed/processed MHC molecules. In the illustrative operation, shift variable 660 can be employed to assist in predicting MHC class-II predictions as described by FIG. 3.

The systems described above can be implemented in whole or in part by electromagnetic signals. These manufactured signals can be of any suitable type and can be conveyed on any type of network. For instance, the systems can be implemented by electronic signals propagating on electronic networks, such as the Internet. Wireless communications techniques and infrastructures also can be utilized to implement the systems.

Figure 7:
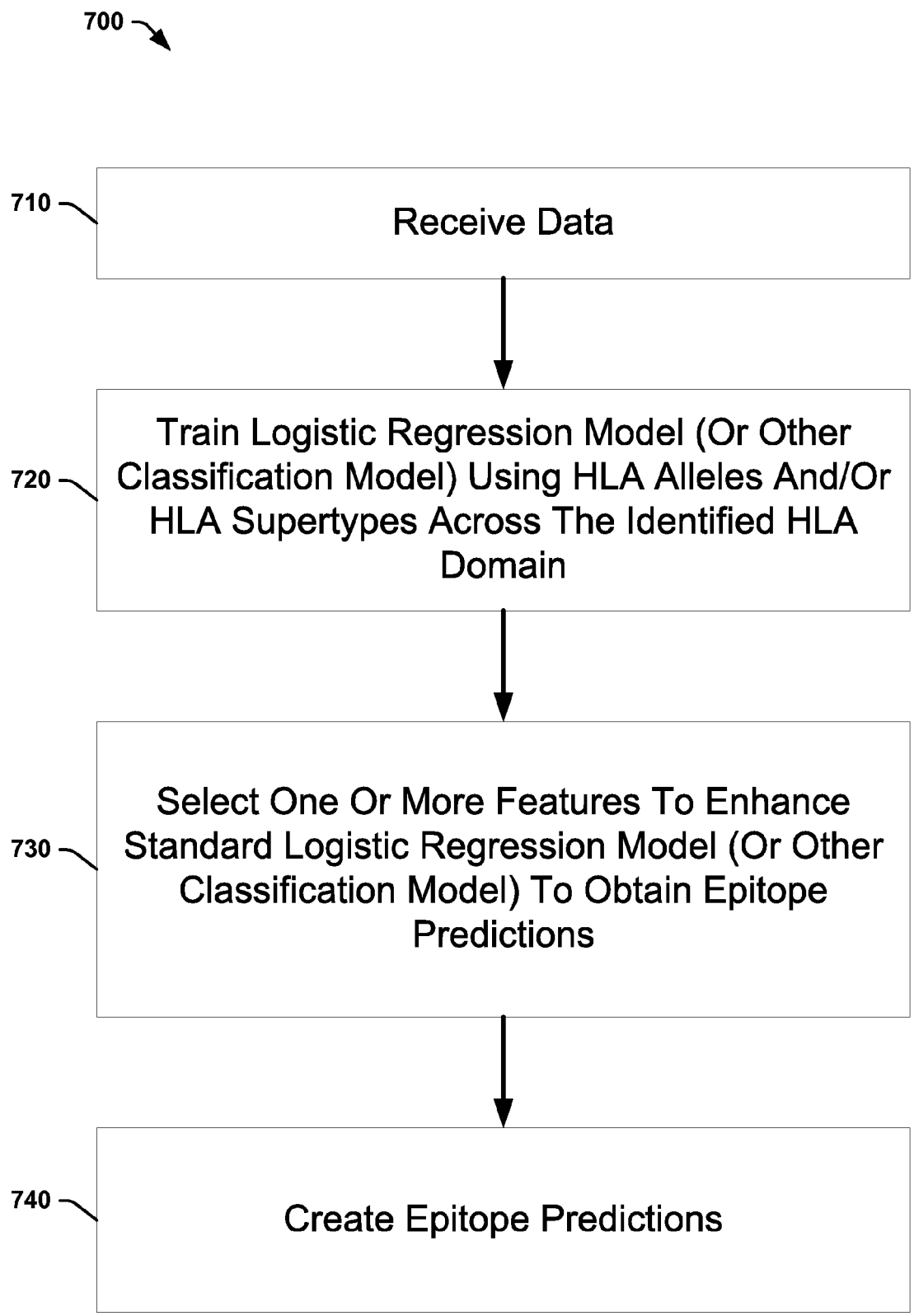
FIG. 7 is a flow diagram of one example of a method of predicting epitopes according to a logistic regression model.

FIG. 7 is a flow diagram of one example of a method 700 of generating an epitope prediction. The method 700 can be encoded by computer-executable instructions stored on computer-readable media. Processing begins at block 710 where data is received for processing at block 720 where a logistic regression (or other classification model) is trained using HLA alleles and/or HLA supertypes across the identified HLA domain. Processing proceeds to block 730 where one or more features to enhance the LR model are selected. In an illustrative implementation such features can include but are not limited to the identity of an amino acid/amino acid chemical property at a given position along either region that flanks the epitope, and the identity of an amino acid/amino acid chemical property at a given position along the MHC molecule. Epitope predictions are then created according to the LR model at block 740.

Figure 8:
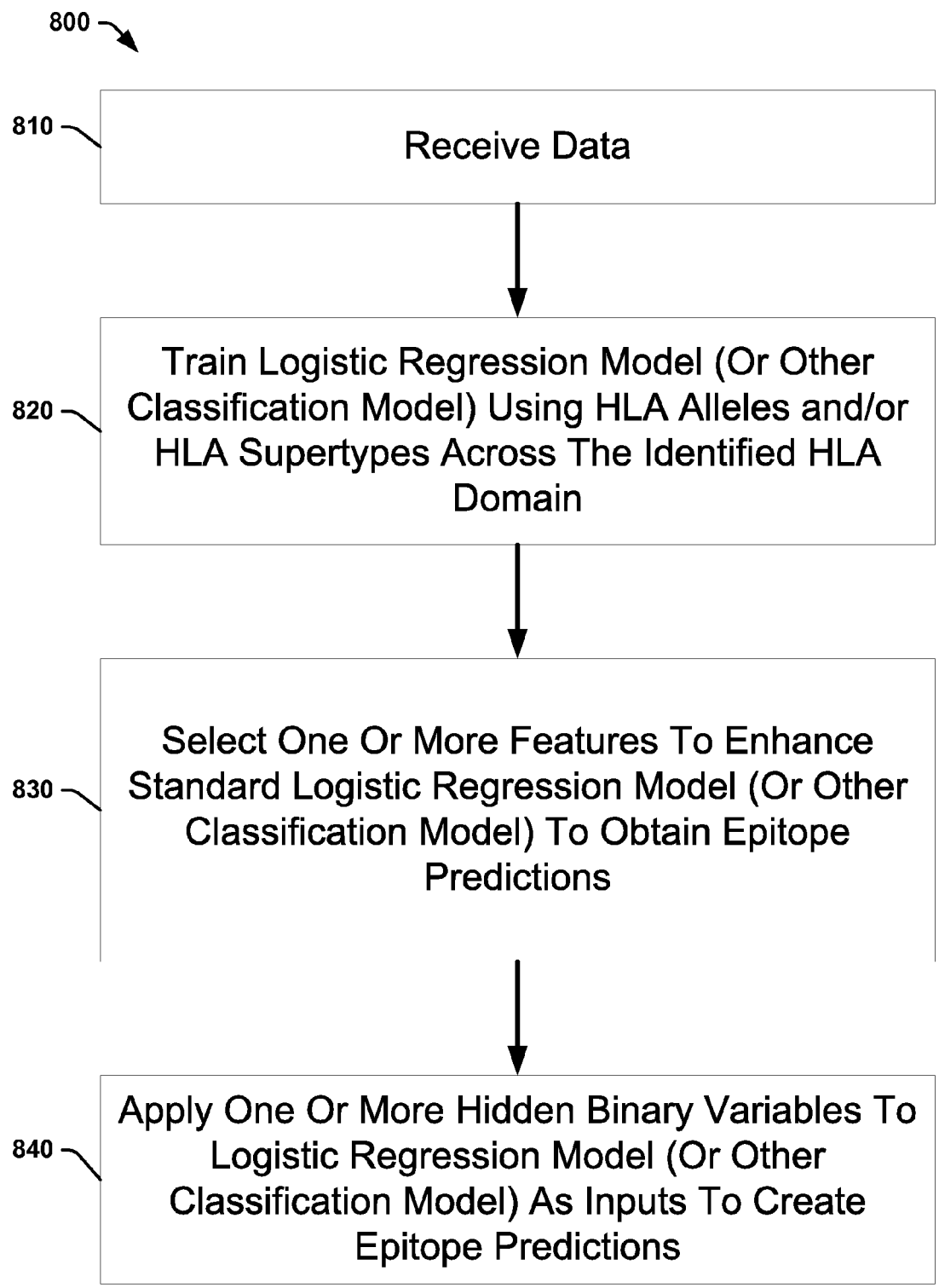
FIG. 8 is a flow diagram of one example of a method of predicting epitopes according to a modified logistic regression model employing hidden variables.

FIG. 8 is a flow diagram of one example of a method 800 for generating an epitope prediction. The method 800 can be encoded by computer-executable instructions stored on computer-readable media. Processing begins at block 810 where data is received for processing at block 820 where a logistic regression (or other classification model) is trained using HLA alleles and/or HLA supertypes across the identified HLA domain. Processing proceeds to block 830 where one or more features to enhance the LR model are selected. In an illustrative implementation such features can include but are not limited to the identity of an amino acid/amino acid chemical property at a given position along either region that flanks the epitope, and the identity of an amino acid/amino acid chemical property at a given position along the MHC molecule. From there processing proceeds to block 840 where one or more hidden binary variables are applied to the LR model as inputs to create desired epitope predictions.

Figure 9:
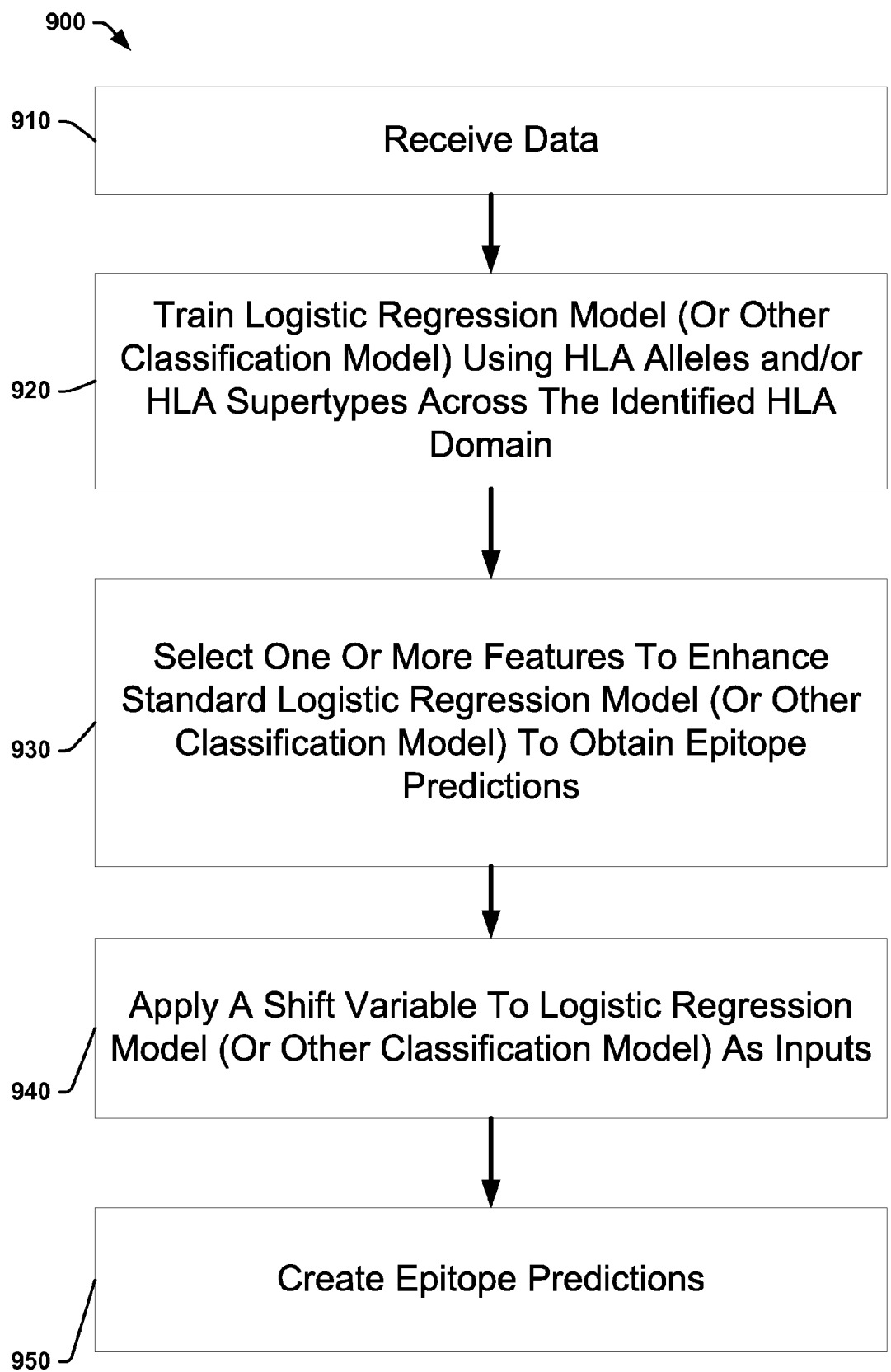
FIG. 9 is a flow diagram of one example of a method of predicting epitopes according another modified logistic regression model employing a shift variable.

FIG. 9 is a flow diagram of one example of a method 900 for generating an epitope prediction. The method 900 can be encoded by computer-executable instructions stored on computer-readable media. Processing begins at block 910 where data is received for processing at block 920 where a logistic regression (or other classification model) is trained using HLA alleles and/or HLA supertypes across the identified HLA domain. Processing proceeds to block 930 where one or more features to enhance the LR model are selected. In an illustrative implementation such features can include but are not limited to the identity of an amino acid/amino acid chemical property at a given position along either region that flanks the epitope, and the identity of an amino acid/amino acid chemical property at a given position along the MHC molecule. From there processing proceeds to block 940 where a shift variable is applied to the LR model as an input. Epitope predictions are then created according to the LR model at block 950.

Figure 10:
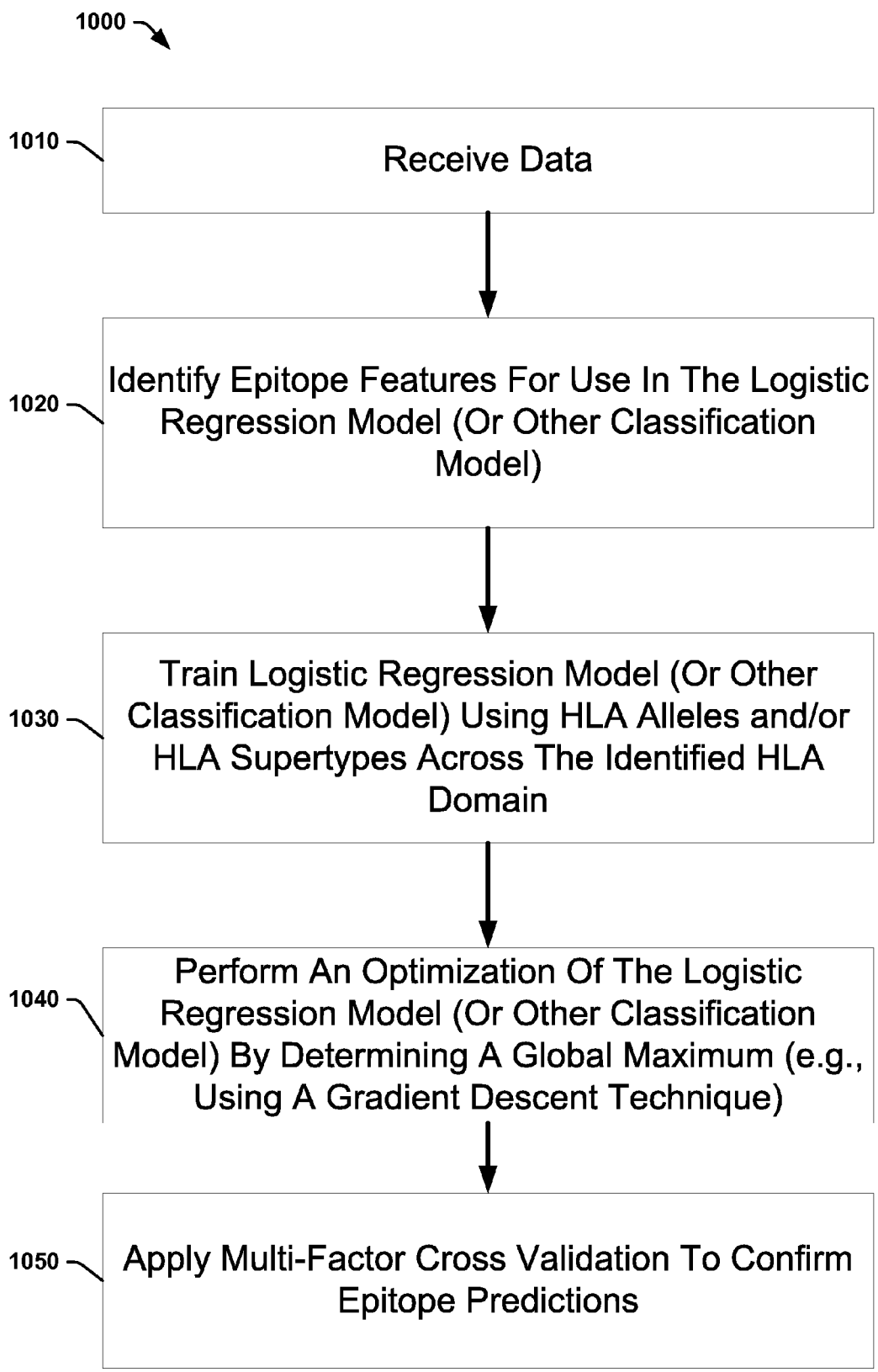
FIG. 10 is a flow diagram of one example of a method of optimizing epitope predictions according to the use of one or more selected features.

FIG. 10 is a flow diagram of one example of a method 1000 of generating an epitope prediction. The method 1000 can be encoded by computer-executable instructions stored on computer-readable media. Processing begins at block 1010 where data is received for processing at blocks 1010 and 1020 where epitope features are identified and a logistic regression (LR) (or other classification model) is trained using HLA alleles and/or HLA supertypes across the identified HLA domain, respectively. An optimization of the LR model is then performed at block 1040 by determining a global maximum. From there, processing proceeds to block 1050 where a multi-factor cross validation is performed to confirm the epitope predictions.

In an illustrative implementation, an exemplary optimization component (not shown) can be utilized to perform the optimization contemplated by block 1040. In the illustrative implementation, the exemplary optimization component can be employed in connection with making determinations or inferences regarding optimization decisions and the like. The optimization component can employ a probabilistic-based or statistical-based approach, for example, in connection with making determinations or inferences. The inferences can be based in part upon explicit training of classifier(s) (not shown) before employing systems 400, 500, and/or 600 of FIGS. 4, 5, and 6, respectively, or implicit training based at least upon previous, or current actions, commands, instructions, and the like during use of the system.

The exemplary optimization component can employ one of numerous methodologies for learning from data and then drawing inferences from the models so constructed (e.g., Hidden Markov Models (HMMs) and related prototypical dependency models, more general probabilistic graphical models, such as Bayesian networks, e.g., created by structure search using a Bayesian model score or approximation, linear classifiers, such as support vector machines (SVMs), non-linear classifiers, such as methods referred to as "neural network" methodologies, fuzzy logic methodologies, and other approaches that perform data fusion, etc.) in accordance with implementing various automated aspects described herein.

Methods also include methods for capture of logical relationships such as theorem provers or more heuristic rule-based expert systems. Inferences derived from such learned or manually constructed models can be employed in optimization techniques, such as linear and non-linear programming, that seek to maximize some objective function.

The optimization component, can take into consideration historical data, and data about current context. Policies can be employed that consider including consideration of the cost of making an incorrect determination or inference versus benefit of making a correct determination or inference. Accordingly, an expected-utility-based analysis can be used to provide inputs or hints to other components or for taking automated action directly. Ranking and confidence measures can be calculated and employed in connection with such analysis.

It should be appreciated that optimization is dynamic and policies selected and implemented will vary as a function of numerous parameters; and thus the optimization component is adaptive. In the illustrative implementation, a gradient descent can be employed to determine the global maximum described in block 1040.

The methods can be implemented by computer-executable instructions stored on one or more computer-readable media or conveyed by a signal of any suitable type. The methods can be implemented at least in part manually. The steps of the methods can be implemented by software or combinations of software and hardware and in any of the ways described above. The computer-executable instructions can be the same process executing on a single or a plurality of microprocessors or multiple processes executing on a single or a plurality of microprocessors. The methods can be repeated any number of times as needed and the steps of the methods can be performed in any suitable order.

The subject matter described herein can operate in the general context of computer-executable instructions, such as program modules, executed by one or more components. Generally, program modules include routines, programs, objects, data structures, etc., that perform particular tasks or implement particular abstract data types. Typically, the functionality of the program modules can be combined or distributed as desired. Although the description above relates generally to computer-executable instructions of a computer program that runs on a computer and/or computers, the user interfaces, methods and systems also can be implemented in combination with other program modules. Generally, program modules include routines, programs, components, data structures, etc. that perform particular tasks and/or implement particular abstract data types.

Moreover, the subject matter described herein can be practiced with most any suitable computer system configurations, including single-processor or multiprocessor computer systems, mini-computing devices, mainframe computers, personal computers, stand-alone computers, hand-held computing devices, wearable computing devices, microprocessor-based or programmable consumer electronics, and the like as well as distributed computing environments in which tasks are performed by remote processing devices that are linked through a communications network. In a distributed computing environment, program modules can be located in both local and remote memory storage devices. The methods and systems described herein can be embodied on a computer-readable medium having computer-executable instructions as well as signals (e.g., electronic signals) manufactured to transmit such information, for instance, on a network.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing some of the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature can be combined with one or more other features of the other implementations of the subject matter as may be desired and advantageous for any given or particular application.

Moreover, it is to be appreciated that various aspects as described herein can be implemented on portable computing devices (e.g., field medical device), and other aspects can be implemented across distributed computing platforms (e.g., remote medicine, or research applications). Likewise, various aspects as described herein can be implemented as a set of services (e.g., modeling, predicting, analytics, etc.).

Figure 11:
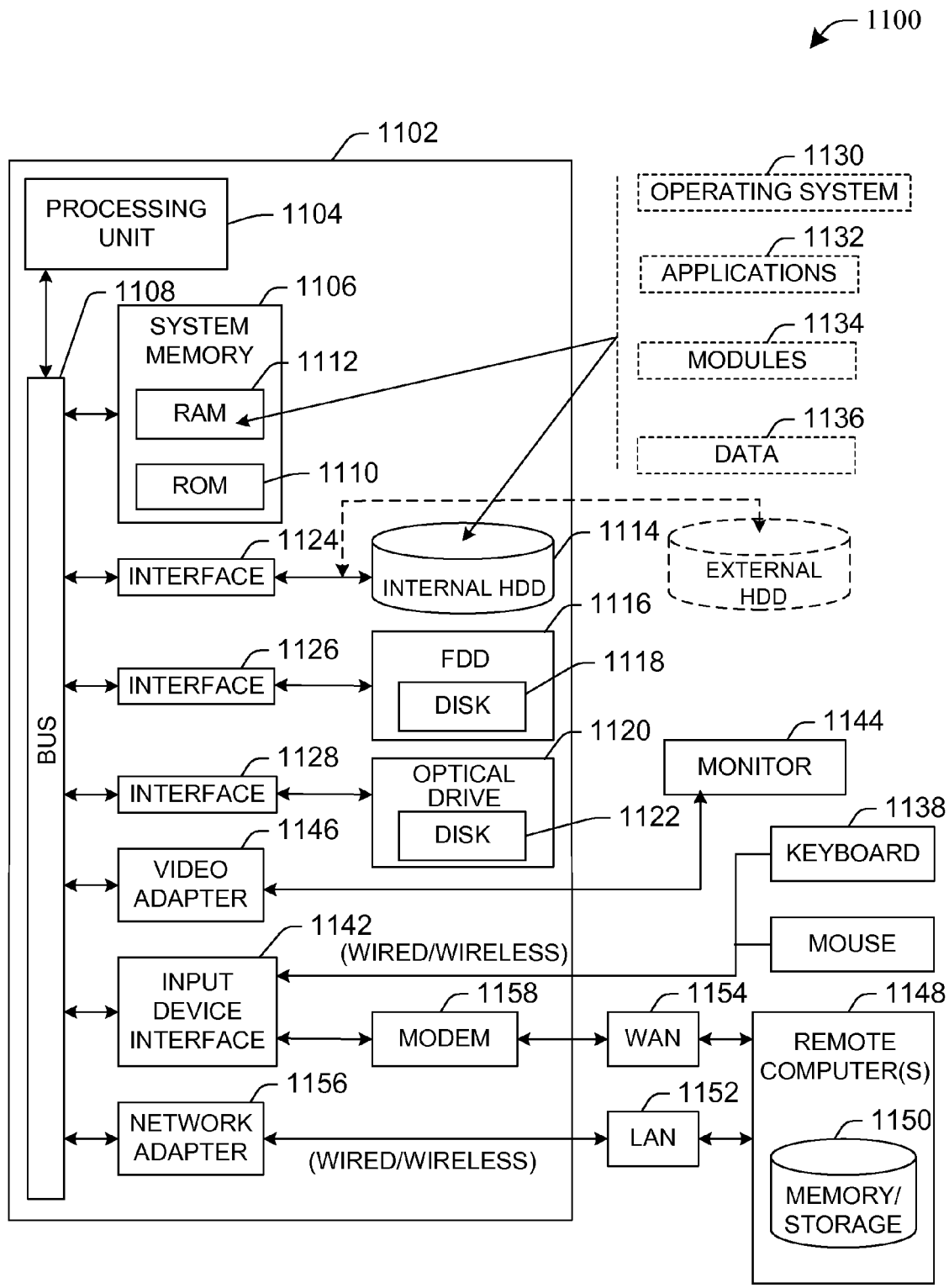
FIG. 11 is an example computing environment in accordance with various aspects described herein.

FIG. 11 illustrates a block diagram of a computer operable to execute the disclosed architecture. In order to provide additional context for various aspects of the subject specification, FIG. 11 and the following discussion are intended to provide a brief, general description of a suitable computing environment 1100 in which the various aspects of the specification can be implemented. While the specification has been described above in the general context of computer-executable instructions that may run on one or more computers, those skilled in the art will recognize that the specification also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the specification may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

More particularly, and referring to FIG. 11, an example environment 1100 for implementing various aspects as described in the specification includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read-only memory (ROM) 1110 and random access memory (RAM) 1112. A basic input/output system (BIOS) is stored in a non-volatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA), which internal hard disk drive 1114 may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE 1394 interface technologies. Other external drive connection technologies are within contemplation of the subject specification.

The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the example operating environment, and further, that any such media may contain computer-executable instructions for performing the methods of the specification.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. It is appreciated that the specification can be implemented with various commercially available operating systems or combinations of operating systems.

A user can enter commands and information into the computer 1102 through one or more wired/wireless input devices, e.g., a keyboard 1138 and a pointing device, such as a mouse 1140. Other input devices (not shown) may include a microphone, an IR remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, an IEEE 1394 serial port, a game port, a USB port, an IR interface, etc.

A monitor 1144 or other type of display device is also connected to the system bus 1108 via an interface, such as a video adapter 1146. In addition to the monitor 1144, a computer typically includes other peripheral output devices (not shown), such as speakers, printers, etc.

The computer 1102 may operate in a networked environment using logical connections via wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices and companies, and facilitate enterprise-wide computer networks, such as intranets, all of which may connect to a global communications network, e.g., the Internet.

When used in a LAN networking environment, the computer 1102 is connected to the local network 1152 through a wired and/or wireless communication network interface or adapter 1156. The adapter 1156 may facilitate wired or wireless communication to the LAN 1152, which may also include a wireless access point disposed thereon for communicating with the wireless adapter 1156.

When used in a WAN networking environment, the computer 1102 can include a modem 1158, or is connected to a communications server on the WAN 1154, or has other means for establishing communications over the WAN 1154, such as by way of the Internet. The modem 1158, which can be internal or external and a wired or wireless device, is connected to the system bus 1108 via the serial port interface 1142. In a networked environment, program modules depicted relative to the computer 1102, or portions thereof, can be stored in the remote memory/storage device 1150. It will be appreciated that the network connections shown are example and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 12:
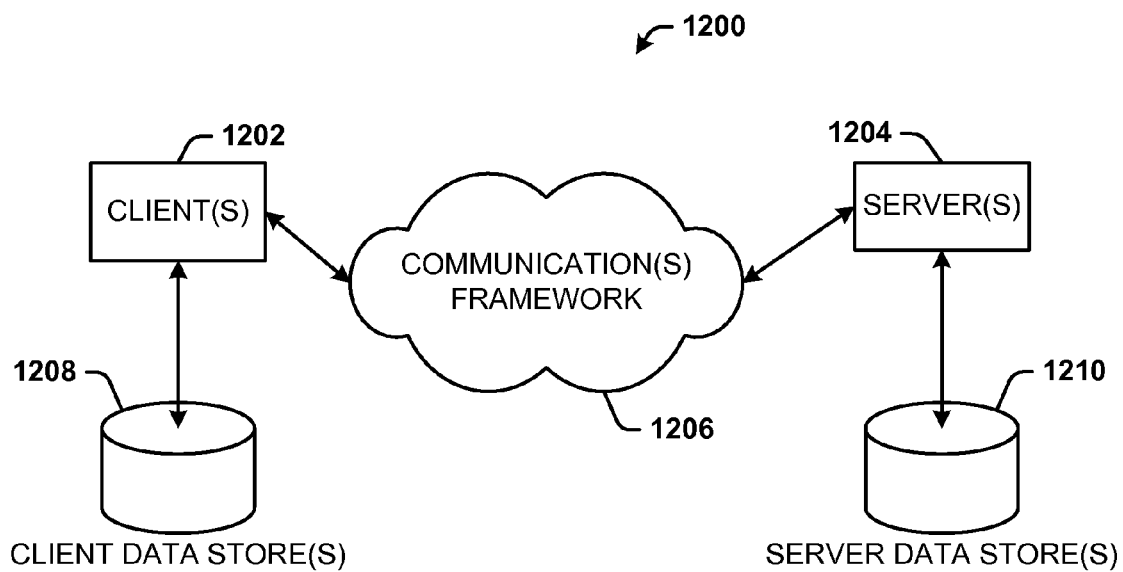
FIG. 12 is an example networked computing environment in accordance with various aspects described herein.

Referring now to FIG. 12, there is illustrated a schematic block diagram of an exemplary computing environment 1200 in accordance with the subject invention. The system 1200 includes one or more client(s) 1202. The client(s) 1202 can be hardware and/or software (e.g., threads, processes, computing devices). The client(s) 1202 can house cookie(s) and/or associated contextual information by employing the subject invention, for example. The system 1200 also includes one or more server(s) 1204. The server(s) 1204 can also be hardware and/or software (e.g., threads, processes, computing devices). The servers 1204 can house threads to perform transformations by employing the subject invention, for example. One possible communication between a client 1202 and a server 1204 can be in the form of a data packet adapted to be transmitted between two or more computer processes. The data packet may include a cookie and/or associated contextual information, for example. The system 1200 includes a communication(s) framework 1206 (e.g., a global communication network such as the Internet) that can be employed to facilitate communications between the client(s) 1202 and the server(s) 1204.

Communications can be facilitated via a wired (including optical fiber) and/or wireless technology. The client(s) 1202 are operatively connected to one or more client data store(s)

1208 that can be employed to store information local to the client(s) 1202 (e.g., cookie(s) and/or associated contextual information). Similarly, the server(s) 1204 are operatively connected to one or more server data store(s) 1210 that can be employed to store information local to the servers 1204.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computer implemented method that facilitates epitope prediction, comprising:
   training, using a processing unit, a logistic regression (LR) model for epitope prediction using information from a plurality of sources representative of standard and special features of a desired epitope,
      wherein the standard features comprise, alone or in conjunction, data representative of an identity and/or supertype of a major histocompatibility complex (MHC) allele, and data representative of the identity and/or a chemical property of an amino acid at a certain position of an epitope,
      wherein the special features comprise, alone or Boolean combinations of, data representative of the standard features, the identity of an amino acid and/or the chemical property of the amino acid at a given position along either region that flanks an epitope and data representative of an amino acid and/or the chemical property of the amino acid at a given position along a MHC molecule;
   employing hidden variables that represent an absence of supertypes among MHC molecules;
   employing a shift variable that represents a position of a peptide within a groove of the MHC molecule; and
   performing a multi-factor cross validation to confirm the epitope prediction.

2. The method as recited in claim 1, further comprising training the LR model on epitopes within HLA alleles and HLA supertypes.

3. A computer readable storage medium having computer readable instructions to instruct a computer to perform a method comprising:
   training a logistic regression (LR) model for epitope prediction using information from a plurality of sources representative of standard and special features of a desired epitope,
      wherein the standard features comprise, alone or in conjunction, data representative of an identity and/or supertype of a major histocompatibility complex (MHC) allele, and data representative of the identity and/or a chemical property of an amino acid at a certain position of an epitope,
      wherein the special features comprise, alone or Boolean combinations of, data representative of the standard features, the identity of an amino acid and/or the chemical property of the amino acid at a given position along either region that flanks an epitope and data representative of an amino acid and/or the chemical property of the amino acid at a given position along a MHC molecule;
   using hidden variables that represent a presence of supertypes among MHC molecules;
   employing a shift variable that represents a position of a peptide within a groove of the MHC molecule; and
   performing a multi-factor cross validation to confirm the epitope prediction.

4. A computer implemented method that facilitates epitope prediction, comprising:
   training, using a processing unit, a logistic regression (LR) model for epitope prediction using one or more hidden variables representative of one or more characteristics of a major histocompatibility complex (MHC) molecule;
   using special features that include an identity of an amino acid and/or a chemical property of the amino acid at a given position along either region that flanks an epitope and the identity of the amino acid and/or the chemical property of the amino acid at a given position along the MHC molecule; and
   performing a multi-factor cross validation to confirm the epitope prediction.

5. The method as recited in claim 4, further comprising identifying the one or more hidden variables representative of a presence of one or more supertypes among MHC molecules.

6. The method as recited in claim 5, further comprising identifying the one or more hidden variables representative of an absence of one or more supertypes among MHC molecules.

7. The method as recited in claim 4, further comprising training the LR model using an expectation-maximization (EM) algorithm wherein a maximization calculus comprises a gradient optimization.

8. The method as recited in claim 7, further comprising determining a probability whether an observed peptide-MHC pair is an epitope using a standard inference.

9. A computer implemented method that facilitates epitope prediction, comprising:
   training, using a processing unit, a logistic regression (LR) model for epitope prediction using one or more shift variables representative of a position of a peptide within a groove of a major histocompatibility complex (MHC) molecule;
   using data representative of an identity of a major histocompatibility complex (MHC) allele and data representative of the identity of an amino acid at a certain position of an epitope; and
   performing a multi-factor cross validation to confirm the epitope prediction.

10. The method as recited in claim 9, further comprising adding a shift variable to the LR model representative of a single position of a peptide within the groove of the MHC molecule.

11. The method as recited in claim 9, further comprising conditioning variables of the LR model on a value of the one or more shift variables.

12. The method as recited in claim 9, further comprising training the LR model using an expectation-maximization (EM) algorithm wherein a maximization calculus comprises a gradient optimization.

13. The method as recited in claim 12, further comprising determining a probability whether an observed peptide-MHC pair is an epitope using a standard interference.

14. A system that facilitates predicting an epitope, the system stored on computer-readable storage media, the system comprising:
- a prediction component configured to predict epitope information by employing information from a plurality of sources including human leukocyte antigen (HLA) alleles and HLA supertypes to be processed by a classification model;
- a classification model engine executing a selected trained classification model employing information using standard and special features of the epitope,
  - wherein the trained classification model is trained to include one or more hidden binary variables that represent a presence or an absence of the HLA supertypes,
  - wherein the trained classification model is trained to include one or more shift variables to generate the epitope prediction,
  - wherein the trained classification model is trained within the HLA alleles and within the HLA supertypes to generate the epitope prediction, and
- the classification model engine further executing the selected trained classification model to perform an optimization by determining a global maximum; and
- the classification model engine further executing the selected trained classification model to perform a multi-factor cross validation to confirm the epitope prediction.

15. The system as recited in claim 14, wherein the classification model comprises a neural network having artificial intelligence capabilities.

16. The system as recited in claim 14, wherein the classification model comprises a logistic regression (LR) model.

17. The system as recited in claim 16, wherein the LR model is given by:

$$\log\frac{p(y|x)}{1-p(y|x)} = w_0 + \sum_{i=1}^{k} w_i \cdot x_i$$

where y=a binary variable to be used for a prediction of whether or not a peptide-HLA pair is an epitope;
where $x=x_1, \ldots, x_k$ is a binary feature to be used for the prediction of whether the features correspond to encodings of properties of the peptide-HLA pair; and
where $w=(w_0, \ldots, w_k)$ are model parameters or weights.

18. The system as recited in claim 17, use a data set of cases $(y^1, x^1), \ldots, (y^n, x^m)$ that are identically distributed given the model parameters, the weights are mutually independent, each having a Gaussian prior $p(w_i|\rho^2)=N(0,\rho^2)$, wherein determining the weights that have the maximum a posteriori (MAP) probability are determined by the quantity:

$$\sum_{j=1}^{n} \log p(y^j|x^j, w) + \sum_{i=0}^{k} \log p(w_i|\sigma^2)$$

where $\rho^2$ can be tuned using a ten-fold cross validation on training data.

19. The system as recited in claim 14, wherein the classification model employs an expectation-maximization (EM) algorithm and a standard inference in determining a probability of whether a given peptide-MHC pair is an epitope.

20. The system as recited in claim 19, wherein a maximization calculus of the EM algorithm comprises a gradient optimization.

* * * * *